US008396551B2

(12) United States Patent  (10) Patent No.: US 8,396,551 B2
Min  (45) Date of Patent: Mar. 12, 2013

(54) SYSTEMS AND METHODS FOR OPTIMIZING VENTRICULAR PACING DELAYS DURING ATRIAL FIBRILLATION

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 654 days.

(21) Appl. No.: 12/507,679

(22) Filed: Jul. 22, 2009

(65) Prior Publication Data

US 2011/0022106 A1    Jan. 27, 2011

(51) Int. Cl.
*A61N 1/00* (2006.01)
*A61B 5/04* (2006.01)

(52) U.S. Cl. .................. 607/5; 607/14; 607/17; 607/18; 607/119; 600/515; 600/516

(58) Field of Classification Search ................ 607/5, 14, 607/17–18, 119; 600/515–516
See application file for complete search history.

(56) References Cited

U.S. PATENT DOCUMENTS

| 6,519,493 | B1 | 2/2003 | Florio et al. | |
|---|---|---|---|---|
| 6,934,585 | B1* | 8/2005 | Schloss et al. | 607/9 |
| 6,996,437 | B2* | 2/2006 | Kramm | 607/9 |
| 7,248,925 | B2 | 7/2007 | Bruhns et al. | |
| 7,308,305 | B1* | 12/2007 | Province et al. | 607/5 |
| 2003/0088285 | A1* | 5/2003 | Marcovecchio et al. | 607/5 |

* cited by examiner

*Primary Examiner* — Nicole F Lavert

(57) ABSTRACT

Techniques are provided for use by implantable medical devices for controlling ventricular pacing, particularly during atrial fibrillation. In one example, during a V sense test for use in optimizing ventricular pacing, the implantable device determines relative degrees of variation within antecedent and succedent intervals detected between ventricular events sensed on left ventricular (LV) and right ventricular (RV) sensing channels. Preferred or optimal ventricular pacing delays are then determined, in part, based on a comparison of the relative degrees of variation obtained during the V sense test. In another example, during RV and LV pace tests, the device distinguishes QRS complexes arising due to interventricular conduction from QRS complexes arising due to atrioventricular conduction from the atria, so as to permit the determination of correct paced interventricular conduction delays for the patient. The paced interventricular conduction delays are also used to optimize ventricular pacing. Biventricular and monoventricular pacing regimes are provided.

15 Claims, 13 Drawing Sheets

SYSTEMS AND METHODS FOR OPTIMIZING VENTRICULAR PACING DELAYS DURING ATRIAL FIBRILLATION

CROSS REFERENCE TO RELATED APPLICATIONS

This application is related to U.S. patent application Ser. No. 12/507,691, filed concurrently herewith, titled "Systems and Methods for Optimizing Ventricular Pacing Delays During Atrial Fibrillation".

FIELD OF THE INVENTION

The invention generally relates to implantable cardiac stimulation devices such as pacemakers and implantable cardioverter-defibrillators (ICDs) and, in particular, to techniques for determining preferred or optimal interventricular (VV) pacing delays for use in pacing the ventricles during episodes of atrial fibrillation (AF) or during asynchronous pacing modes.

BACKGROUND OF THE INVENTION

Clinical studies related to cardiac pacing have shown that an optimal atrio-ventricular pacing delay (e.g., AV delay or PV delay) and/or an optimal interventricular pacing delay (e.g., VV delay) can improve cardiac performance. However, such optimal delays depend on a variety of factors that may vary over time. Thus, what is "optimal" may vary over time. An optimization of AV/PV pacing delay and/or VV pacing delay may be performed at implantation and sometimes, a re-optimization may be performed during a follow-up consultation. While such optimizations are beneficial, the benefits may not last due to changes in various factors related to device and/or cardiac function.

The following patents and patent applications set forth various systems and methods for allowing a pacemaker, implantable cardioverter-defibrillator (ICD) or other cardiac rhythm management (CRM) device to determine and/or adjust AV/PV/VV pacing delays so as to help maintain the pacing delays at optimal values: U.S. patent application Ser. No. 10/703,070, filed Nov. 5, 2003, entitled "Methods for Ventricular Pacing"; U.S. patent application Ser. No. 10/974,123, filed Oct. 26, 2004; U.S. patent application Ser. No. 10/986,273, filed Nov. 10, 2004; U.S. patent application Ser. No. 10/980,140, filed Nov. 1, 2004; U.S. patent application Ser. No. 11/129,540, filed May 13, 2005; U.S. patent application Ser. No. 11/952,743, filed Dec. 7, 2007. See, also, U.S. patent application Ser. No. 12/328,605, filed Dec. 4, 2008, entitled "Systems and Methods for Controlling Ventricular Pacing in Patients with Long Intra-Atrial Conduction Delays" and U.S. patent application Ser. No. 12/132,563, filed Jun. 3, 2008, entitled "Systems and Methods for determining Intra-Atrial Conduction Delays using Multi-Pole Left Ventricular Pacing/Sensing Leads." See, further, U.S. Pat. No. 7,248,925, to Bruhns et al., entitled "System and Method for Determining Optimal Atrioventricular Delay based on Intrinsic Conduction Delays." At least some of the techniques are implemented within the QuickOpt™ systems of St. Jude Medical.

In particular, techniques were set forth within at least some of these patent documents for exploiting various inter-atrial and interventricular conduction delays to determine preferred or optimal AV/PV/VV pacing delays. Techniques were also set forth for exploiting the VV delays to determine which ventricles should be paced—the left ventricle (LV), the right ventricle (RV), both ventricles, or neither, and in which order. In at least some examples, the implanted device (or an external programming device in communication with the implanted device) performs a series of tests to determine intrinsic AV/PV and VV conduction delays from which preferred pacing delays are determined. In particular, an "A sense" test is performed to detect intrinsic intra-atrial delays from which preferred AV/PV pacing delays are determined. A "V sense" test is performed to detect intrinsic ventricular events from which an intrinsic interventricular conduction delay ($\Delta$) is determined. An "RV pace" test and a separate "LV pace" test are performed to detect paced interventricular conduction delays (IVCD_RL and IVCD_LR, respectively) from which an intrinsic interventricular correction term ($\epsilon$) is determined. The optimal VV delay for use in biventricular pacing is then set based on $\Delta$ and $\epsilon$.

Issues can arise, though, if the patient is subject to an ongoing episode of AF. During AF, the atria of the heart beat chaotically, resulting in irregular AV conduction. As such, it can be difficult to determine values for $\Delta$ and $\epsilon$. For example, due to the irregular AV conduction, the V sense test might not be able to reliably determine the order in time of sensed LV and RV QRS complexes and hence might not be able to reliably determine the value of $\Delta$. (A QRS complex is a portion of an intracardiac electrogram that represents intrinsic ventricular depolarization. Within biventricular systems, separate LV and RV QRS complexes can be detected on respective LV and RV sensing channels.)

Accordingly, some aspects of the invention are directed to providing improved V sense test techniques for use during AF to allow for a reliable determination of $\Delta$ despite irregular AF conduction for use in determining optimal VV pacing delays.

Another concern during AF is that the implanted device typically needs to switch to a non-atrial tracking mode (such as VVI, V00, D00) for delivering RV and LV pacing pulses. During a non-atrial tracking mode, it can be difficult to reliably perform the LV pace and RV pace tests to determine values for IVCD_RL and IVCD_LR for use in setting the VV pacing delay. One particular concern is that, during the LV and RV pace tests, QRS complexes can arise in a given ventricular chamber either due to interventricular conduction from the other chamber (triggered by RV or LV pulses) or due to AV conduction from the atria (triggered by atrial P-waves.) An inability to distinguish between these events makes it difficult to reliably determine values for IVCD_RL and IVCD_LR for use in determining $\epsilon$ and setting VV.

Accordingly, other aspects of the invention are directed to providing improved RV pace and LV pace test techniques for use during non-atrial tracking modes to allow for a reliable determination of IVCD_RL and IVCD_LR values for use in determining optimal VV pacing delays.

SUMMARY OF THE INVENTION

In a first general exemplary embodiment, a method is provided for controlling the delivery of cardiac pacing therapy by an implantable cardiac rhythm management device for use with patients subject to AF. Briefly, a degree of variation is determined within "antecedent" intervals ($\Delta-$) between ventricular events sensed by the device on a first channel (such as the RV channel) and preceding ventricular events sensed on a second channel (such as the LV channel). A degree of variation is also determined within "succedent" intervals ($\Delta+$) between ventricular events sensed on the first channel and subsequent ventricular events sensed on the second channel. Ventricular pacing is then controlled, at least in part, based on a comparison of the two degrees of variation.

In one embodiment, the device is a pacemaker equipped for biventricular pacing. During AF, the device performs a V sense test to detect an intrinsic interventricular conduction delay (Δ) for determining optimal or preferred VV pacing delays for use during AF. During the test, the device detects LV QRS complexes within an LV intracardiac electrogram (LV-IEGM) sensed using an LV lead (implanted via the coronary sinus) and also detects RV QRS complexes within an RV-IEGM sensed using an RV lead. Due to irregular AV conduction during AF, the relative order of the LV and RV QRS complexes is not initially known and is determined based on a comparison of the relative degrees of variation in the two sets of intervals (Δ–,Δ+).

More specifically, during the V sense test, the device determines a degree of variation in the Δ– intervals (herein VAR (Δ–)) and also determines a degree of variation in the Δ+ intervals (herein VAR(Δ+)). The degrees of variation may be determined, for example, based on standard deviations. The device then compares the degree of variation in the Δ– intervals to the degree of variation in the Δ+ intervals to determine which has a smaller degree of variation (e.g. the greater degree of regularity.) The intrinsic interventricular conduction delay (Δ) of the patient is then derived from the set of intervals having the smaller degree of variation. For example, if VAR(Δ–) is smaller than VAR(Δ+), Δ is set equal to negative |Δ–|. Conversely, if VAR(Δ+) is smaller than VAR(Δ–), Δ is instead set equal to positive |Δ+|. In this manner, the device determines the true order of the LV and RV QRS complexes, such that the true intrinsic interventricular conduction delay (Δ) of the patient can be determined by the V sense test.

The device then performs separate RV pace and LV pace tests to determine paced interventricular conduction delays (IVCD_RL and IVCD_LR). In one example, the device performs the RV pace test by first detecting RR intervals between RV QRS complexes on the RV channel. The device then sets an RV pacing interval for delivering a sequence of RV pacing pulses to the RV of the patient, where the RV pacing interval is set shorter than substantially most of the RR intervals detected on the RV channel (such as shorter than 95% to 98% of the RR intervals detected on the RV channel.) The helps ensure that most of the resulting LV QRS complexes will arise via interventricular conduction from the RV and not via AV conduction from the atria. Techniques for directly distinguishing LV QRS's arising via interventricular conduction from LV QRS's arising via AV conduction are summarized below. Having set the RV pacing interval, the device then delivers a sequence of RV pacing pulses, detects LV QRS's and detects the time delays from the RV pulses to the LV QRS's. The IVCD_RL is then determined based on the time delays from RV pulses to the LV QRS's, such as by averaging a set of such time delays together to yield the value for IVCD_RL. A similar procedure is performed using LV pulses to complete the LV pace test to determine IVCD_LR.

The device then determines the interventricular correction term (ε) from IVCD_RL and IVCD_LR by subtracting IVCD_RL from IVCD_LR. The interventricular pacing delay (VV) is then set based on:

$VV = \alpha_1(\Delta+\epsilon)$, where $\alpha_1$ is 0.5 (or other suitable coefficient) with $\Delta = -|\Delta-|$ if var(Δ–)<var(Δ+); and $\Delta = |\Delta+|$ if var(Δ–)>var(Δ+).

Biventricular pacing is then delivered to the patient during AF using VV. The sign of VV determines which ventricular chamber is to be paced first. If VV is positive, the RV is paced first; otherwise the LV is paced first.

Alternatively, monoventricular pacing is instead delivered to the patient during AF, triggered by a sensed QRS complex in the opposing chamber as determined based on the relative degrees of variation in the Δ– and Δ+ intervals. In one example, if the degree of variation in the Δ– intervals is smaller than the degree of variation in the Δ+ intervals, then upon detection of a sensed QRS in the LV, a ventricular pacing pulse is immediately delivered to the RV. Conversely, if the degree of variation in the Δ+ intervals is smaller than the degree of variation in the Δ– intervals, then upon detection of a sensed QRS in the RV, a ventricular pacing pulse is immediately delivered to the LV.

In a second general exemplary embodiment, a method is provided for controlling the delivery of cardiac pacing therapy by an implantable cardiac rhythm management device during an atrial non-tracking mode such as VVI or various asynchronous modes. Briefly, ventricular pacing pulses are delivered to a selected ventricular chamber (such as the RV). Candidate QRS complexes (which may also be referred to as "paced propagations") are detected within the other ventricular chamber (such as the LV). The device then distinguishes QRS complexes arising due to interventricular conduction from QRS complexes arising due to AV conduction from the atria by, for example, comparing the candidate QRS complexes against a suitable template. A paced interventricular conduction delay (e.g., IVCD_RL or IVCD_LR) is then determined based on measured time delays between the ventricular pacing pulses and the QRS complexes that have been identified as arising due to interventricular conduction. Ventricular pacing is then controlled, at least in part, based on the paced interventricular conduction delay.

In one example, the device performs both an RV pace test to determine IVCD_RL and an LV pace test to determine IVCD_LR. During the RV pace test, only LV QRS complexes arising due to interventricular conduction from the RV are used for determining the value of IVCD_RL. During the LV pace test, only RV QRS complexes arising due to interventricular conduction from the LV are used for determining the value of IVCD_LR. More particularly, for the RV pace test, the device delivers RV pulses and detects candidate LV QRS complexes on the LV channel. The device compares the candidate LV QRS complexes against a template representative of an LV QRS arising due to AV conduction. If the candidate LV QRS complex matches the LV QRS template indicative of AV conduction, then the candidate LV QRS is rejected. If, however, the candidate LV QRS complex does not match the template, then the candidate is accepted as being an LV QRS complex that arose due to interventricular conduction. Alternatively, the template can be defined to represent the shape of a LV QRS complex due to paced interventricular conduction (in which case the candidate event is accepted if it matches the template, and is rejected otherwise.)

Once LV QRS complexes arising due to interventricular conduction are distinguished from those due to AV conduction, the device determines the IVCD_RL based on the time delays from RV pulses to their corresponding LV QRS complexes. Similar procedures are performed using LV pulses to complete the LV pace test to determine IVCD_LR. The interventricular pacing delay (VV) for the patient is then set based on an interventricular correction term (ε) derived from IVCD_RL and IVCD_LR and an intrinsic interventricular conduction delay (Δ) derived from a suitable V sense test, such as the one as summarized above.

System and method implementations of these techniques are presented herein.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
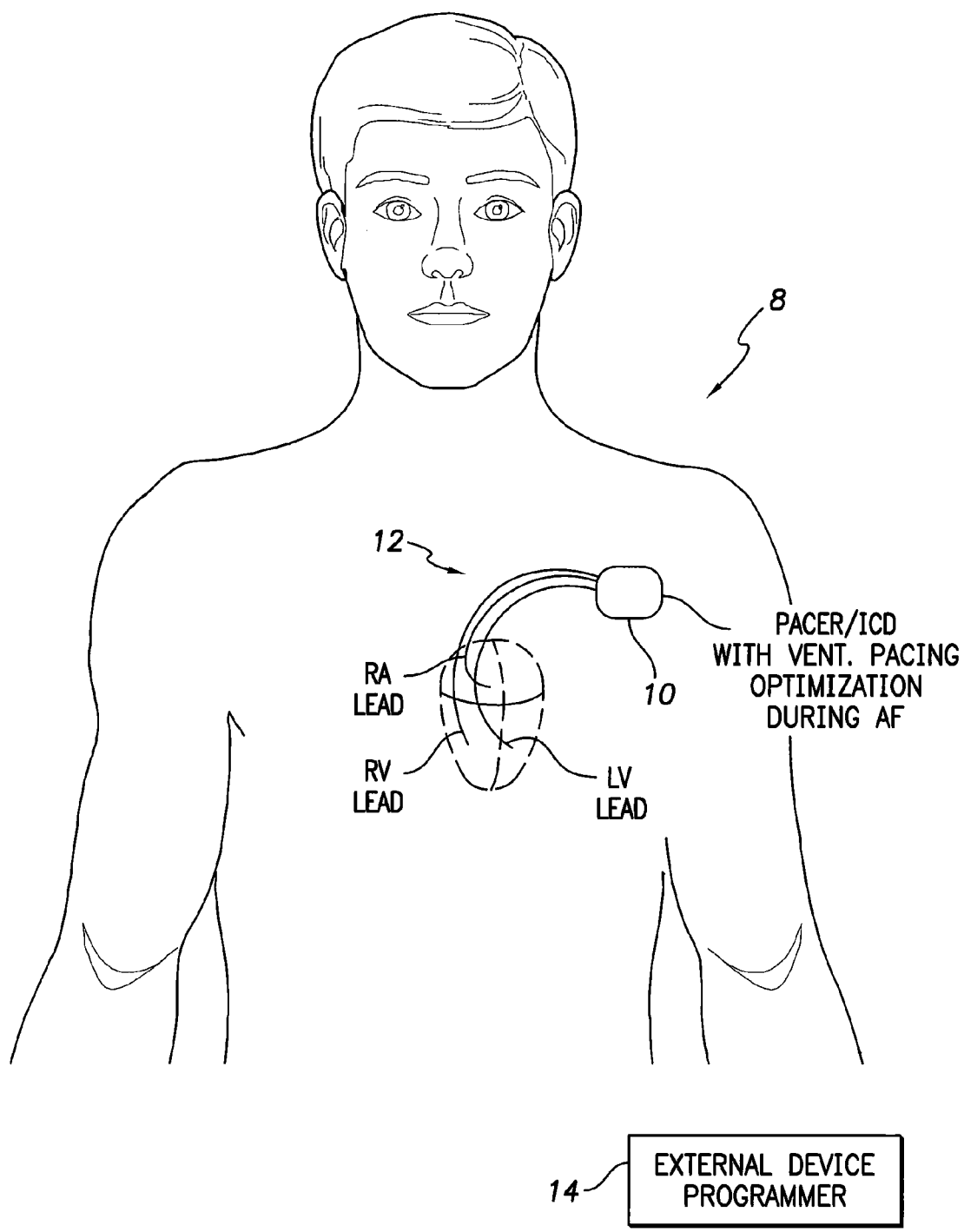
FIG. 1 illustrates pertinent components of an implantable medical system having a pacemaker or ICD capable of optimizing ventricular pacing delays during AF or during any non-atrial tracking mode.

FIG. 1 illustrates an implantable medical system 8 capable of performing a rapid optimization of ventricular pacing parameters during AF. The medical system 8 includes a pacer/ICD 10 or other cardiac rhythm management device equipped with one or more cardiac sensing/pacing leads 12 implanted within the heart of the patient. In FIG. 1, a stylized representation of the leads is provided. A more complete and accurate illustration of a set of leads is provided in FIG. 11. In some implementations, the pacer/ICD itself performs the optimization based on electrocardiac signals sensed using the leads. In other implementations, the device transmits features of the electrocardiac signals to an external device programmer 14 that performs the optimization. That is, the device programmer determines the optimal ventricular pacing parameters, which are then programmed into the pacer/ICD via telemetry. Other external devices might instead be used to perform the optimization, such as bedside monitors or the like. In some embodiments, the device programmer or bedside monitor is directly networked with a centralized computing system, such as the HouseCall™ system or the Merlin@home/Merlin.Net systems of St. Jude Medical.

In the following examples, it is assumed that the pacer/ICD performs the optimization using on-board components. An example where the external programmer performs the optimization is described below with reference to FIG. 13. As will be explained, different forms of optimization can be performed and various examples are set forth in FIGS. 2-10.

Interval-Based Ventricular Pacing Optimization During AF

Figure 2:
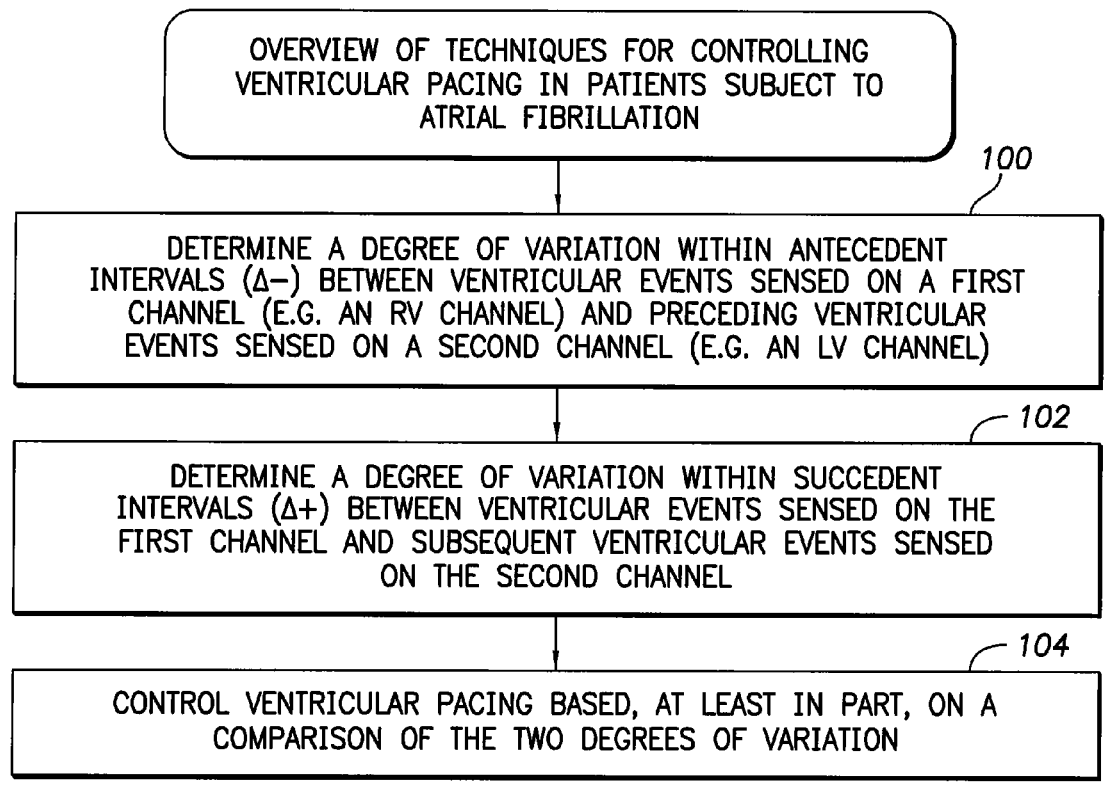
FIG. 2 is a flowchart providing an overview of a technique for controlling ventricular pacing during AF based on relative degrees of variation in Δ− and Δ+ intervals, which may be performed by the system of FIG. 1.

FIG. 2 broadly summarizes a general technique for controlling ventricular pacing parameters during AF that may be exploited by the pacer/ICD of FIG. 1 or other suitably equipped systems. Beginning at step 100, the pacer/ICD determines a degree of variation within intervals (Δ−) between ventricular events sensed on a first channel (e.g. an RV channel) and preceding ventricular events sensed on a second channel (e.g. an LV channel). These intervals may be referred to as antecedent intervals. At step 102, the pacer/ICD determines a degree of variation within intervals (Δ+) between ventricular events sensed on the first channel and subsequent ventricular events sensed on the second channel. These intervals may be referred to as succedent intervals. At step 104, the pacer/ICD then controls ventricular pacing based, at least in part, on a comparison of the degrees of variation obtained from the antecedent and succedent intervals (Δ−,Δ+). For example, the degrees of variation of the antecedent and succedent intervals (Δ−,Δ+) may be compared to determine which has the smaller degree of variation (i.e. the greater degree of regularity). VV pacing delays for use in controlling biventricular pacing can then be determined, in part, based on an interventricular conduction delay (Δ) determined using the intervals having the smaller degree of variation. Alternatively, monoventricular pacing can be controlled by using the intervals having the smaller degree of variation to determine the chamber to receive the monoventricular pacing pulses (i.e. RV vs. LV.)

The general technique of FIG. 2 can be exploited during AF or at any time when the device is pacing in a non-atrial tracking mode, such as VVI, V00 or D00. Typically, upon detection of AF based on a high atrial rate, the device performs a "mode switch" to a non-atrial tracking mode (especially VVI) so that the irregularity of the atrial beats during AF does not interfere with delivery of ventricular pacing. VVI indicates that the device is capable of pacing and sensing in the ventricles and also inhibiting functions based upon events sensed in the ventricles, but does not respond to atrial events. V00 and D00 are asynchronous pacing modes where pacing pulses are not synchronized with either atrial or ventricular events. To exploit the technique of FIG. 2 for sensing RV and LV QRS (with no V pacing), temporarily program to VVI with rate of 40 bpm or program to ODO mode (i.e. sensing only.)

Figure 3:
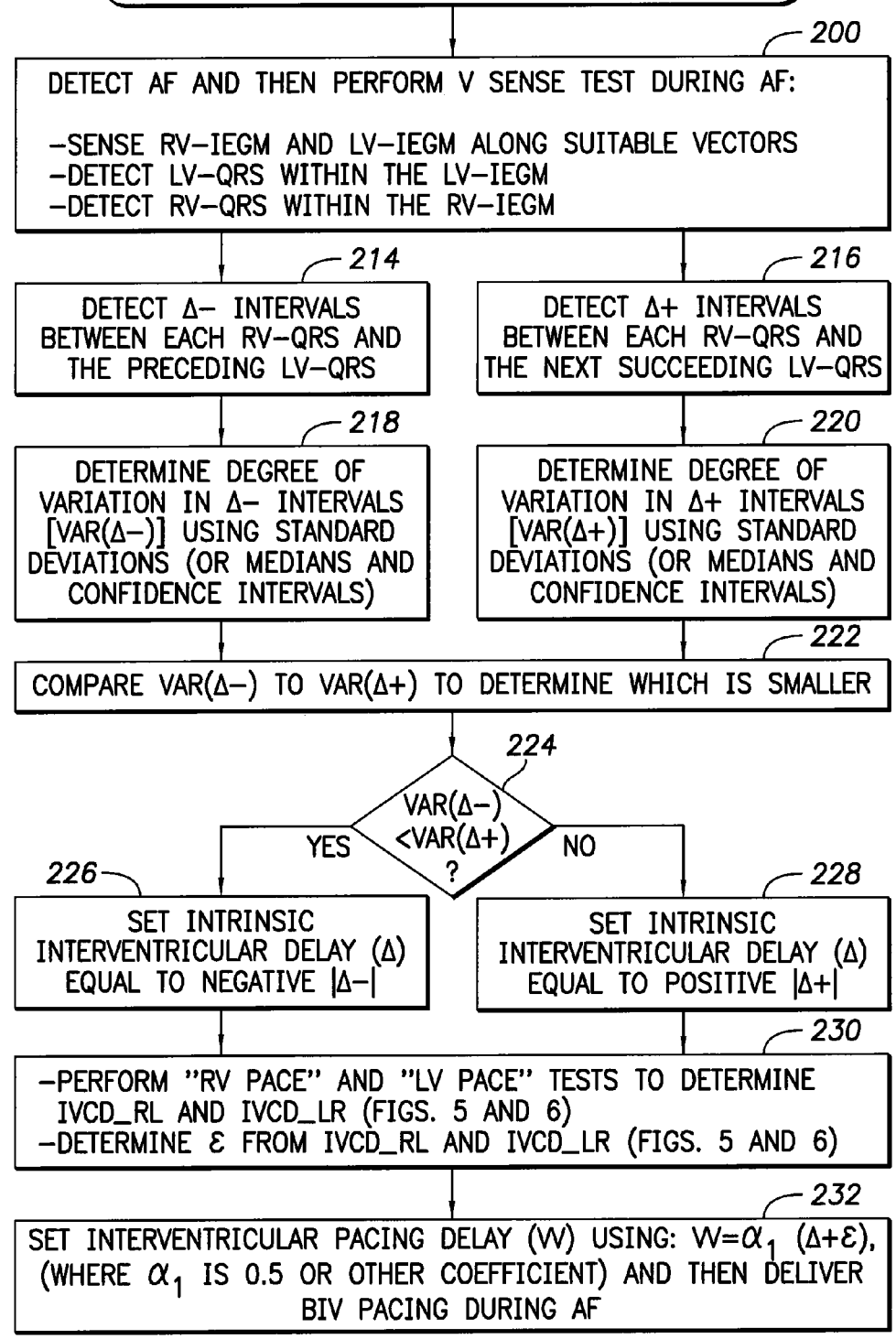
FIG. 3 is a flowchart illustrating an exemplary biventricular implementation of the technique of FIG. 2 wherein relative degrees of variation in the Δ− and Δ+ intervals are used to determine optimal biventricular pacing delays.

FIG. 3 provides a more detailed example wherein biventricular pacing is controlled during AF. Beginning at step 200, the pacer/ICD detects AF and then performs a V sense test during AF. It should be understood that, within at least some patients, AF occurs more or less continuously and unabated. In other patients, individual episodes of AF occur from time to time, some lasting well over a week. In either case, the presence of AF can be detected and confirmed based on an examination of the atrial rate and/or based on an analysis of P-wave intervals and morphology within an atrial IEGM (A-IEGM) obtained via an RA lead. In one example, if the atrial rate exceeds a threshold value such as 150 beats per minute (bpm), AF is assumed.

During the V sense test of step 200, the pacer/ICD: senses RV-IEGM and LV-IEGM signals along suitable sensing vectors; detects LV-QRS events within the LV-IEGM; and detects RV-QRS events within the RV-IEGM. Exemplary RV and LV IEGMs are shown in FIG. 4 (in stylized form).

Figure 4:
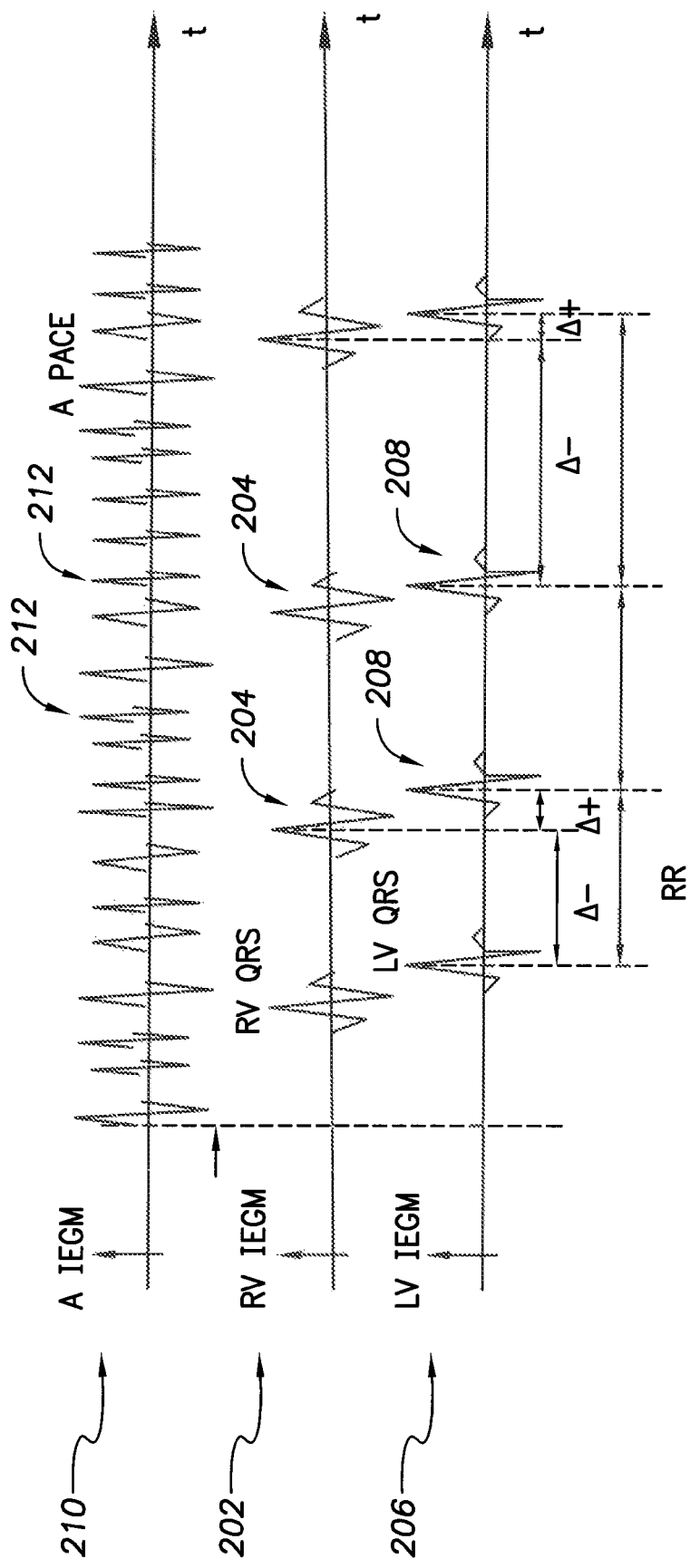
FIG. 4 is a graph illustrating an exemplary A-IEGM, RV-IEGM and LV-IEGM during AF, and particularly illustrating the Δ− and Δ+ intervals exploited by the techniques of FIGS. 2-3.

More specifically, FIG. 4 illustrates an RV IEGM 202 having a set of RV QRS complexes 204 and an LV IEGM 206 having a set of LV QRS complexes 208. For the sake of completeness, FIG. 4 also provides an exemplary A-IEGM 210 having a set of irregular P-waves 212. It should be understood, however, that for the purposes of performing the V sense test of step 200 of FIG. 3, the A-IEGM need not be analyzed. It is sufficient to analyze the RV and LV IEGMs. Note that the irregular occurrence of the P-waves in the atria causes irregular intervals between the RV and LV QRS complexes due to AV conduction of the irregular P-waves. As such, the relative order of the RV and LV QRS complexes is not necessarily clear. Hence, it may not be clear whether a given RV QRS corresponds to the LV QRS that precedes it or the LV QRS that follows. As such, it is not immediately clear what intervals should be measured to determine the intrinsic interventricular conduction delay ($\Delta$) for use in setting VV pacing intervals.

Returning to FIG. 3, to determine the correct value for $\Delta$, at step 214, the pacer/ICD detects a set of $\Delta-$ intervals, with each individual $\Delta-$ interval measured between a given RV-QRS in the RV IEGM and the immediately preceding LV-QRS in the LV IEGM. Exemplary $\Delta-$ intervals are identified in FIG. 4. In this example, the $\Delta-$ intervals are measured between the peaks of the QRS complexes. Other points within the QRS could instead be used in other implementations to measure the intervals. A sufficient number of $\Delta-$ intervals are detected to permit evaluating a degree of variation in the intervals. For example, $\Delta-$ intervals are detected and recorded over a predetermined period of time (such as over one minute) or for a predetermined number of ventricular beats (such as more than for eight beats.) Concurrently, at step 216, the pacer/ICD detects a set of $\Delta+$ intervals, with each individual $\Delta+$ interval measured between a given RV-QRS in the RV IEGM and the immediately succeeding LV-QRS in the LV IEGM. Exemplary $\Delta+$ intervals are also shown in FIG. 4. As with the $\Delta-$ intervals, a sufficient number of $\Delta+$ intervals are detected during the test to permit evaluating a degree of variation in the intervals.

At step 218 of FIG. 3, the pacer/ICD determines the degree of variation in the $\Delta-$ intervals [which is represented herein as VAR($\Delta-$)]. The degree of variation can be determined using standard deviations. That is, the pacer/ICD examines the set of $\Delta-$ intervals detected and recorded at step 214 and determines the standard deviation within the intervals. The smaller the standard deviation, the smaller the degree of variation in the intervals. Alternatively, the pacer/ICD can determine the median and then count the number of intervals occurring within a range surrounding the median defined by $\pm X$ % where X is a predetermined value such as 5-10 subject to a confidence interval of 95%. The greater the number of intervals within that range, the smaller the degree of variation in the intervals. Other variation determination techniques can also be used. Concurrently, at step 220, the pacer/ICD also determines the degree of variation in the $\Delta+$ intervals [which is represented herein as VAR($\Delta+$)]. Again, the degree of variation can be determined using standard deviations or other suitable techniques.

At step 222, the pacer/ICD compares VAR($\Delta-$) to VAR($\Delta+$) to determine which is smaller. For example, the device compares the standard deviation in $\Delta-$ to the standard deviation in $\Delta+$. If VAR($\Delta-$) is less than VAR($\Delta+$), as determined at step 224, then the device concludes at step 226 that $\Delta-$ represents the true interventricular conduction delay within the patient. That is, the LV is depolarizing first (in response to electrical signals received via the AV), then the RV is depolarizing. Accordingly, $\Delta$ is set equal to negative $|\Delta-|$. (The negative value is used to indicate that the LV depolarizes first, i.e. the RV QRS to LV QRS interval is negative.) Conversely, if VAR($\Delta-$) is greater than or equal to VAR($\Delta+$), then the device concludes at step 228 that $\Delta+$ represents the true interventricular conduction delay within the patient. That is, the RV is depolarizing first, then the LV is depolarizing. Accordingly, $\Delta$ is set equal to $|\Delta+|$.

The set of intervals having the smaller degree of variations is deemed to represent the true interventricular conduction delay since it exhibits a greater degree of regularity. In this regard, time delays between the LV and RV should be fairly consistent, even during AF, resulting in a small degree of variation in the intervals between LV and RV QRS complexes both triggered by the same P-wave. However, since P-waves are typically quite irregular during AF, there can be significant variations in the intervals between an LV QRS triggered by one P-wave and the RV QRS triggered by a different P-wave. In any case, regardless of the medical explanation for the differences in interval variations, the selection of the interval having the smaller degree of variation is preferred herein for the purposes of determining $\Delta$.

Having determined $\Delta$, the pacer/ICD at step 230 then performs "RV pace" and "LV pace" tests to determine IVCD_RL and IVCD_LR values for use in calculating the intrinsic interventricular correction term ($\epsilon$), which is used along with $\Delta$ to set VV (the interventricular pacing delay for use during biventricular pacing.) The RV and LV pace tests are described below with reference to FIGS. 5-6.

At step 232, the pacer/ICD sets the interventricular pacing delay (VV) using:

$$VV = \alpha_1(\Delta + \epsilon)$$

where $\alpha_1$ is 0.5 or other predetermined coefficient. Also, at step 232, the pacer/ICD delivers biventricular pacing during AF using VV. Alternatively, monoventricular pacing is delivered, with the chamber receiving the ventricular pacing pulse selected based on the sign of ($\Delta$), as will be described with reference to FIG. 7.

As to the coefficient, $\alpha_1$ is a programmable or hard-coded parameter that may vary from patient to patient. In some examples, $\alpha_1$ is set to 0.5, which may also be used as a default value. Otherwise routine testing may be used to determine preferred or optimal values for $\alpha_1$ based, e.g., on an evaluation of the resulting hemodynamics within test patients.

Thus, FIG. 3 illustrates an exemplary technique for determining an optimal or preferred value for VV. It should be understood that this value is not necessarily truly optimal in any particular quantifiable sense. As can be appreciated, what constitutes a truly "optimal" value depends on the criteria used for judging the resulting performance, which can be subjective in the minds of some clinicians. The value for VV set at step 232 is, nevertheless, at least a preferred value for use in pacing. Clinicians may choose to adjust this value via device programming for particular patients, at their discretion.

Figure 5:
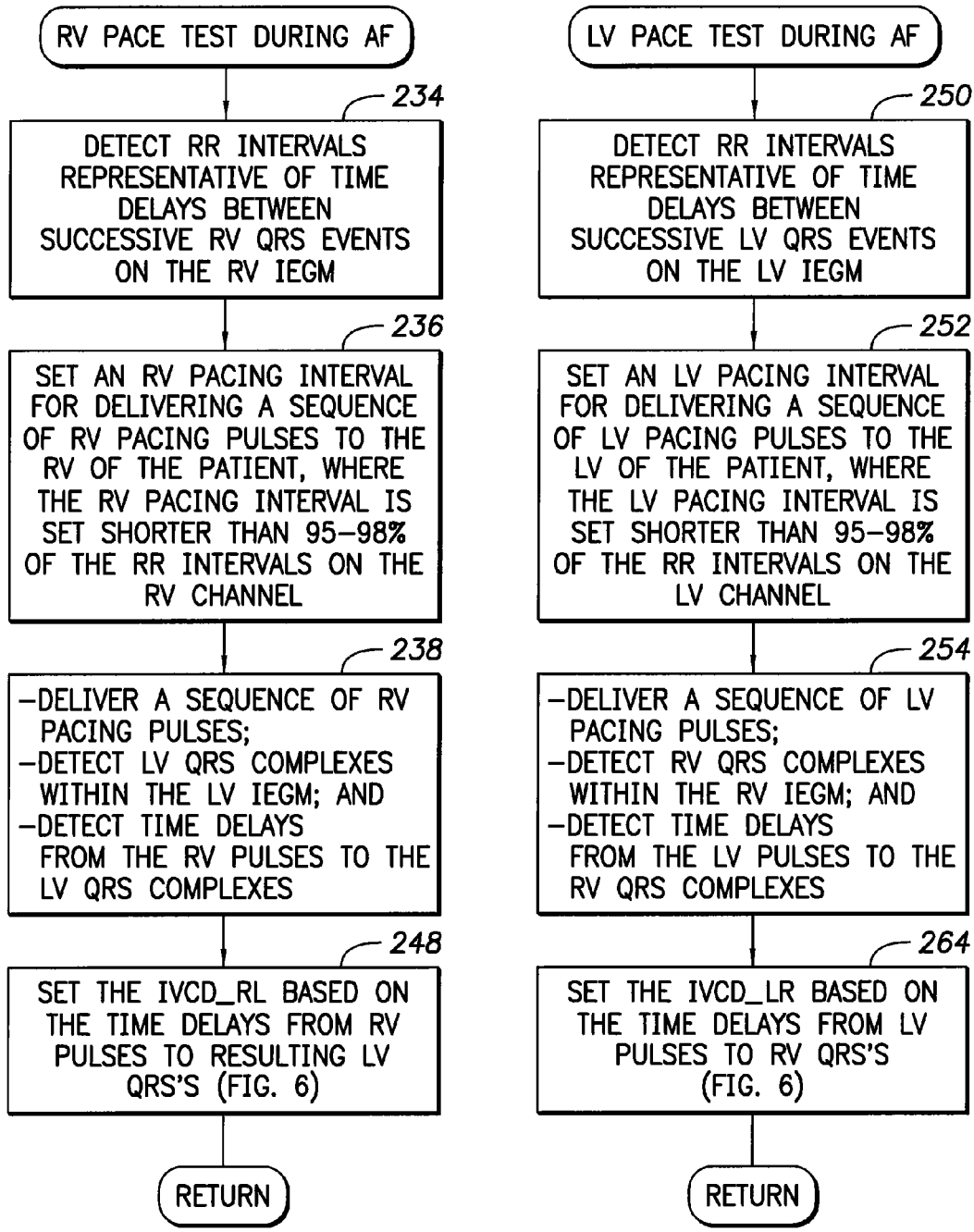
FIG. 5 is a flowchart exemplary techniques for performing RV pace and LV pace tests for use with the implementation of FIG. 3, wherein RR intervals are exploited in setting RV and LV pacing intervals during the test.
Figure 6:
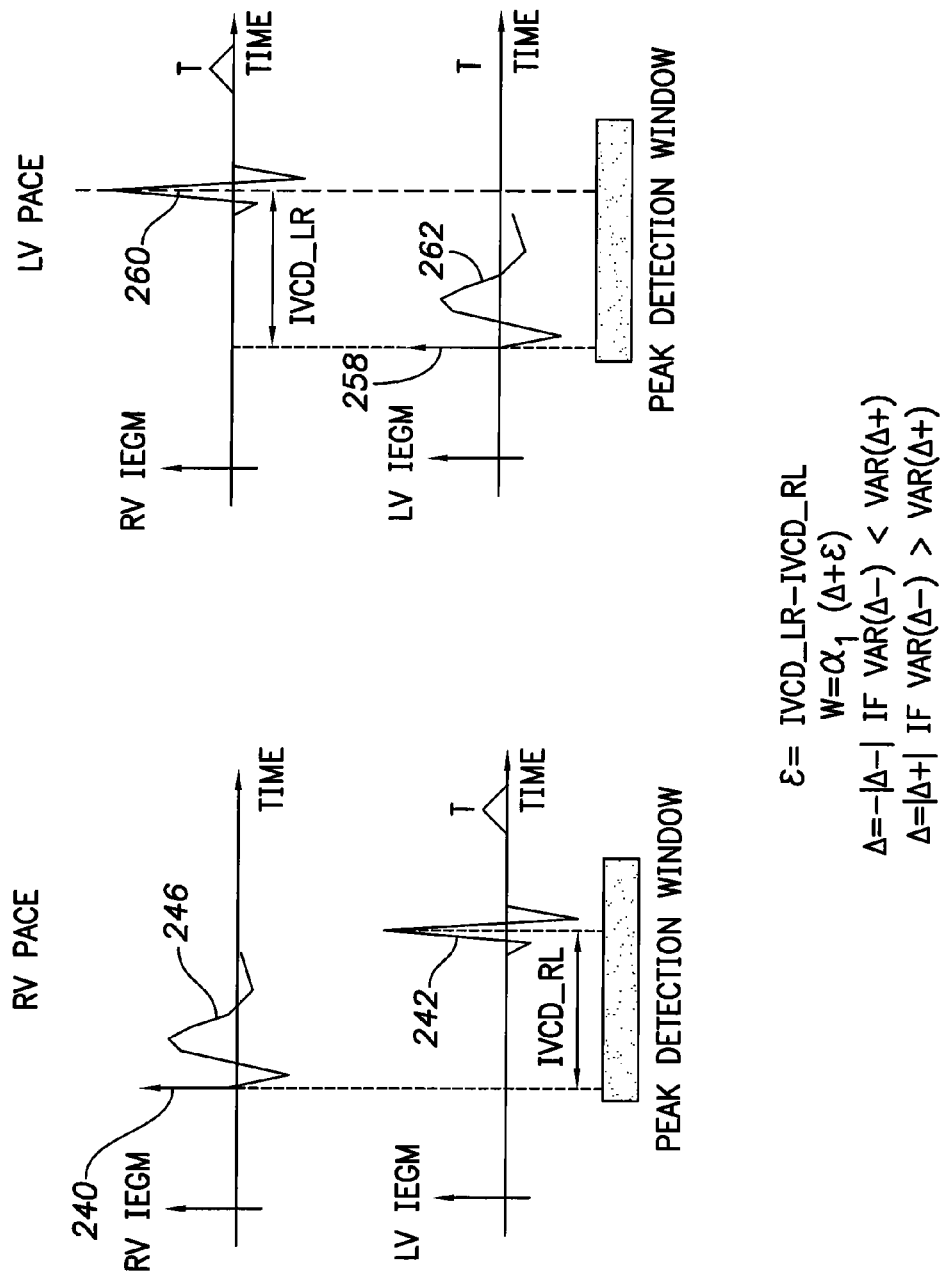
FIG. 6 is a graph illustrating LV and RV IEGMs sensed during the RV and LV pace tests of FIG. 5.

Turning now to FIGS. 5-6, techniques for performing RV and LV pace tests will be described. These tests determine values for IVCD_RL and IVCD_LR for use in determining the intrinsic interventricular correction term ($\epsilon$), which is used along with $\Delta$ to set VV (as already explained.)

For an RV pace test, beginning at step 234 of FIG. 5, the pacer/ICD detects and records RR intervals on the RV IEGM or LV IEGM, which are representative of time delays between successive intrinsic RV QRS events. That is, at this point, RV pacing has not yet been initiated. Due to the possible irregularity of the intrinsic RV QRS or LV QRS complexes during AF, the duration of the RR intervals may vary significantly from one RV QRS to another (as shown in FIG. 4.) Accordingly, the device preferably collects and records RR intervals over a sufficiently large number of RV QRS or LV QRS events, such as over a period of one minute or for an interval having at least sixty ventricular beats, to obtain a representative average.

At step 236, the pacer/ICD sets an RV pacing interval for delivering a sequence of RV pacing pulses to the RV of the patient, where the RV pacing interval is set shorter than 95-98% of the RR intervals detected at step 234. This helps ensure that a substantial majority of the RV pulses to be delivered during the RV pace test will be captured by the RV or dominate or over drive RV pacing so that no AF beats can be conducted.

At step 238, the pacer/ICD then performs the RV pace test by: delivering a sequence of RV pacing pulses using to the RV pacing interval determined at step 236; detecting responsive LV QRS complexes on an LV channel; and detect time delays from the RV pulses to the LV QRS's.

FIG. 6 illustrates the delivery of an RV pulse 240 during an RV pace test and the resulting LV QRS 242 on an LV IEGM channel. The interval between the RV pulse and the peak of the LV QRS is the IVCD_RL, which may vary somewhat from beat to beat over the course of the RV pace test. Preferably, a sequence of RV pulses are delivered over a period of at least one minute or during an interval at least eight RV pulses so as to measure and record a set of IVCD_RL values from which an average can be derived. FIG. 6 also illustrates an RV ER 246 on the RV IEGM channel. The ER may be detected so as to verify capture of the RV pulse and, if necessary, the RV pulse magnitude can be increased to compensate for any persistent lack of capture.

Returning to FIG. 5, at step 250, the pacer/ICD then sets the IVCD_RL based on the average time delays from the RV pulses to the resulting LV QRS events.

Similar steps are performed for an LV pace test. Briefly, beginning at step 250 of FIG. 5, the pacer/ICD detects and records RR intervals on the LV IEGM. At step 252, the pacer/ICD sets an LV pacing interval, where the LV pacing interval is set shorter than 95-98% of the RR intervals detected at step 250. At step 254, the pacer/ICD then performs the LV pace test by: delivering a sequence of LV pacing pulses; detecting responsive RV QRS complexes on the RV channel; and detecting time delays from the LV pulses to the RV QRS's.

FIG. 6 illustrates the delivery of an LV pulse 258 during an LV pace test and the resulting RV QRS 260 on the RV IEGM channel. Again, preferably, a sequence of pulses are delivered over a period of at least one minute or during an interval at least eight RV pulses so as to measure and record a set of IVCD_LR values from which an average can be derived. FIG. 6 also illustrates an LV ER 262 on the LV IEGM channel, which may be detected to verify capture. Returning to FIG. 5, at step 264, the pacer/ICD then sets the IVCD_LR based on the average time delays from the LV pulses to the resulting RV QRS's.

Figure 7:
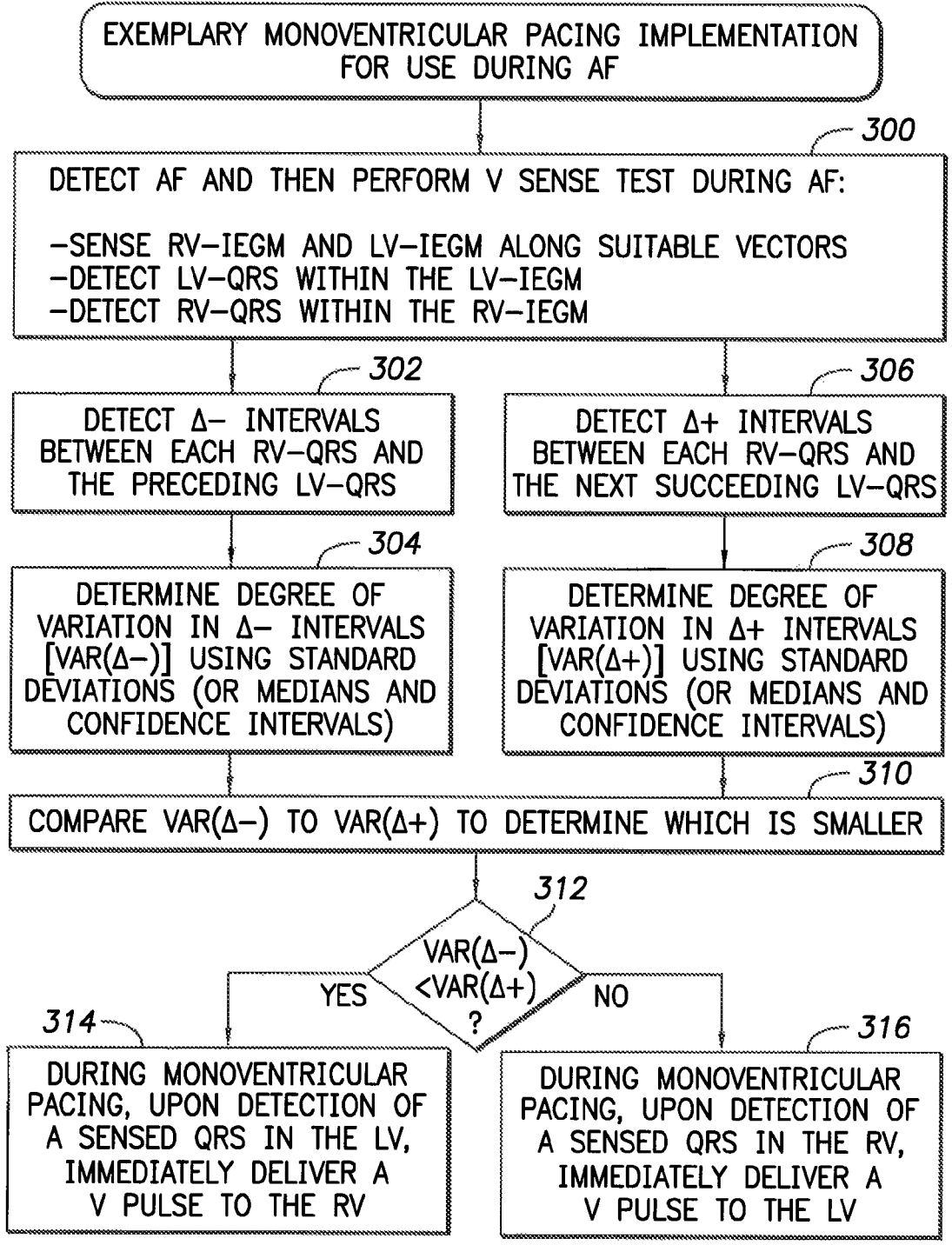
FIG. 7 is a flowchart illustrating an exemplary monoventricular implementation of the technique of FIG. 3 wherein relative degrees of variation in the Δ− and Δ+ intervals are used to determine which ventricular chamber to pace.

Turning now to FIG. 7, monoventricular pacing techniques will be described that exploit the $\Delta+$, $\Delta-$ intervals to determine which chamber to pace. Some of the steps of FIG. 7 are the same or similar to those of FIG. 3 and hence will not be described again in detail. Beginning at step 300, the pacer/ICD detects AF and then performs a V sense test during AF (during which the device senses RV-IEGM and LV-IEGM signals; detects LV-QRS events within the LV-IEGM; and detects RV-QRS events within the RV-IEGM.)

At step 302, the pacer/ICD detects a set of $\Delta-$ intervals and, at step 304, determines the degree of variation in the $\Delta-$ intervals [i.e. VAR($\Delta-$)]. Concurrently, at step 306, the pacer/ICD detects a set of $\Delta+$ intervals and, at step 308, determines the degree of variation in the $\Delta+$ intervals [i.e. VAR($\Delta+$)]. At step 310, the pacer/ICD compares VAR($\Delta-$) to VAR($\Delta+$) to determine which is smaller. If VAR($\Delta-$) is less than VAR($\Delta+$), as determined at step 312, then the device concludes at step 314 that $\Delta$ is negative. Accordingly, during monoventricular pacing, upon detection of a sensed QRS in the LV, the device will immediately deliver a V-PULSE to the RV. Conversely, if VAR($\Delta-$) is not less than VAR($\Delta+$), the device concludes at step 316 that $\Delta$ is positive. Accordingly, during monoventricular pacing, upon detection of a sensed QRS in the RV, the device will immediately deliver a V-PULSE to the LV. Since monoventricular pacing is to be delivered, there is no need to calculate VV and hence no need to evaluate IVCD_LR or IVCD_RL.

Template-Based Techniques for Use During Non-Atrial Tracking Modes

Figure 8:
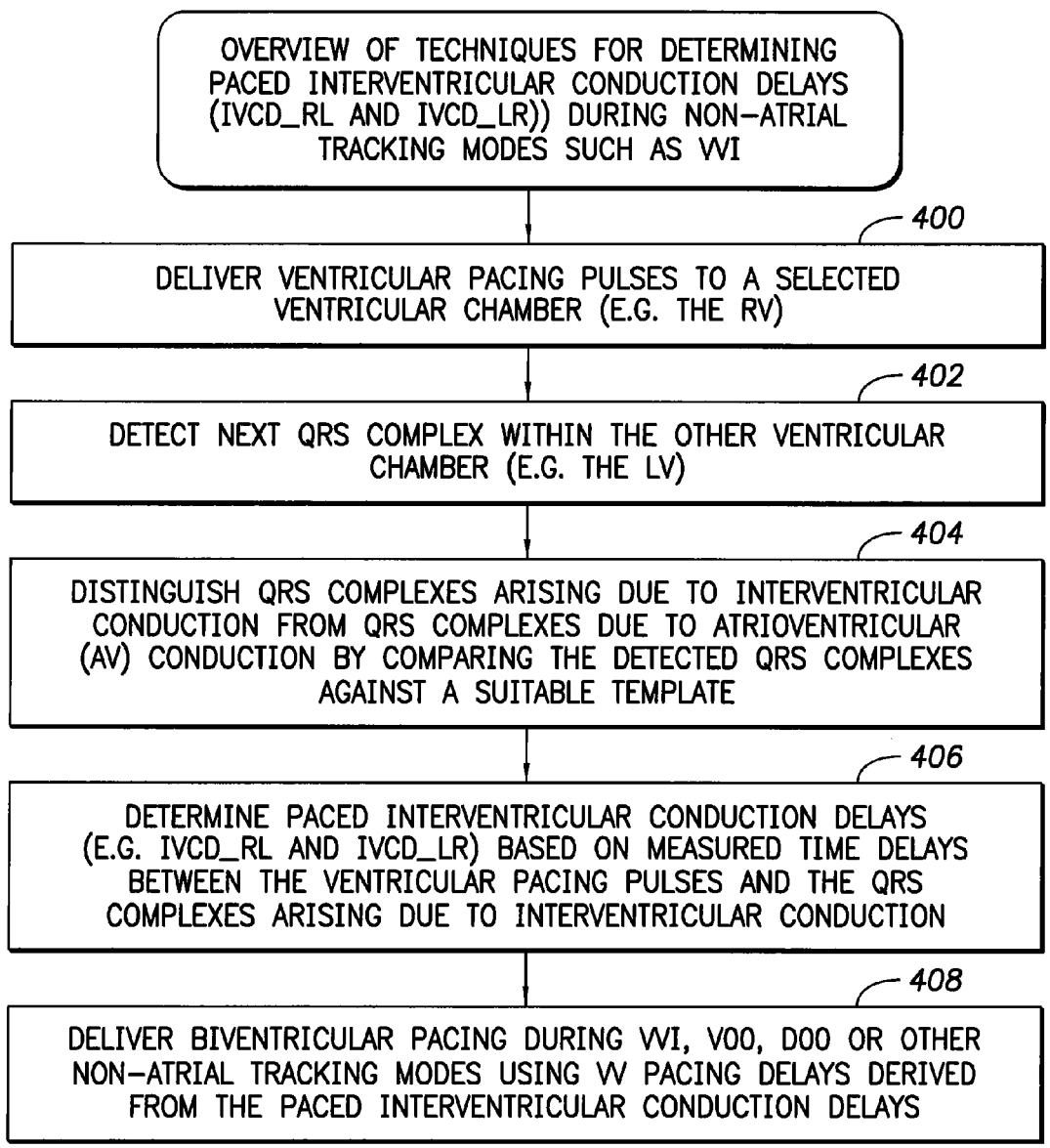
FIG. 8 is a flowchart providing an overview of a technique for controlling ventricular pacing during an atrial non-tracking mode (such as VVI) that employs template-matching to distinguish QRS complexes arising due to interventricular conduction from those arising due to AV conduction, which may be performed by the system of FIG. 1.
Figure 9:
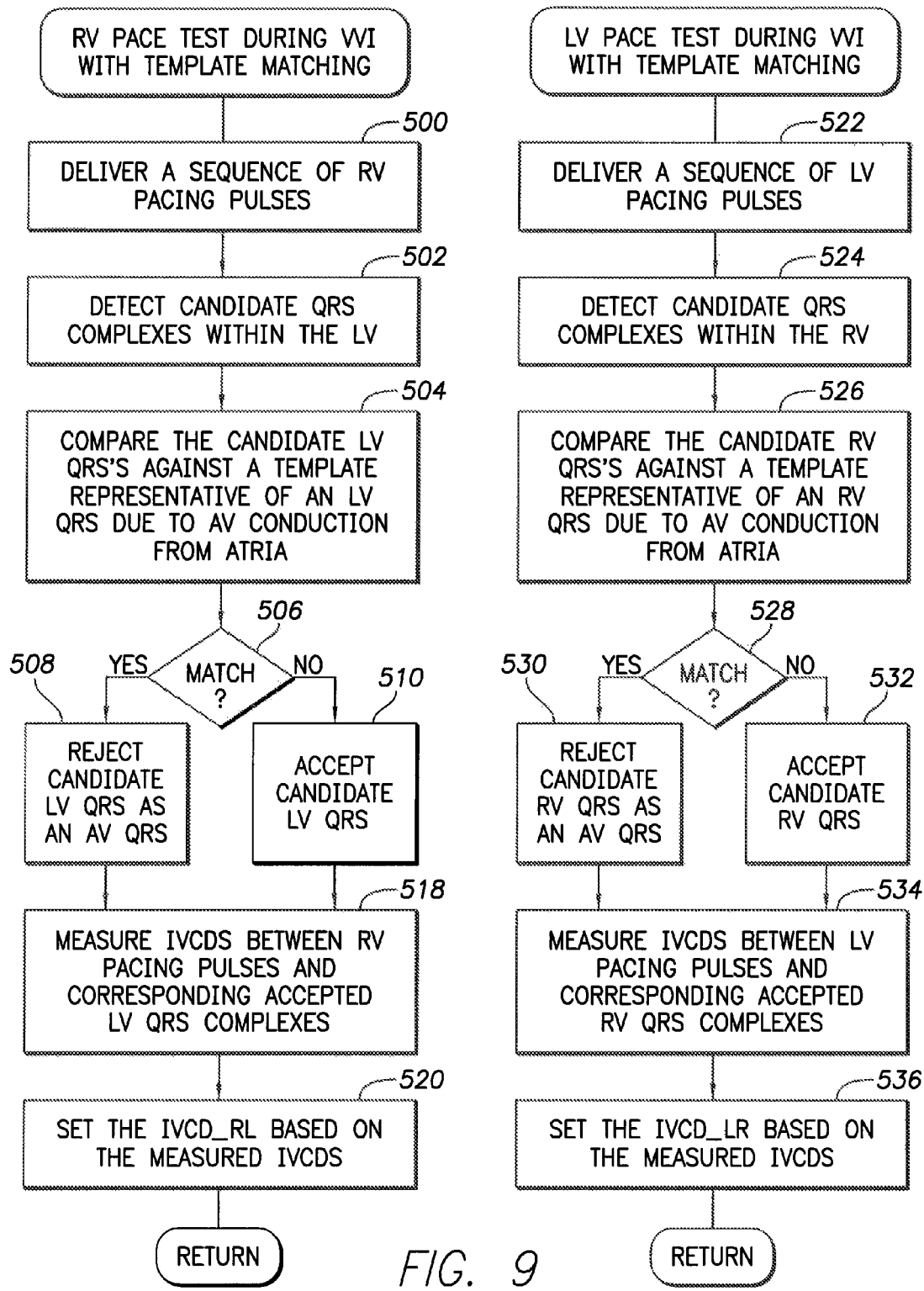
FIG. 9 is a flowchart illustrating an exemplary biventricular implementation of the technique of FIG. 8 wherein separate RV and LV pace tests are performed.
Figure 10:
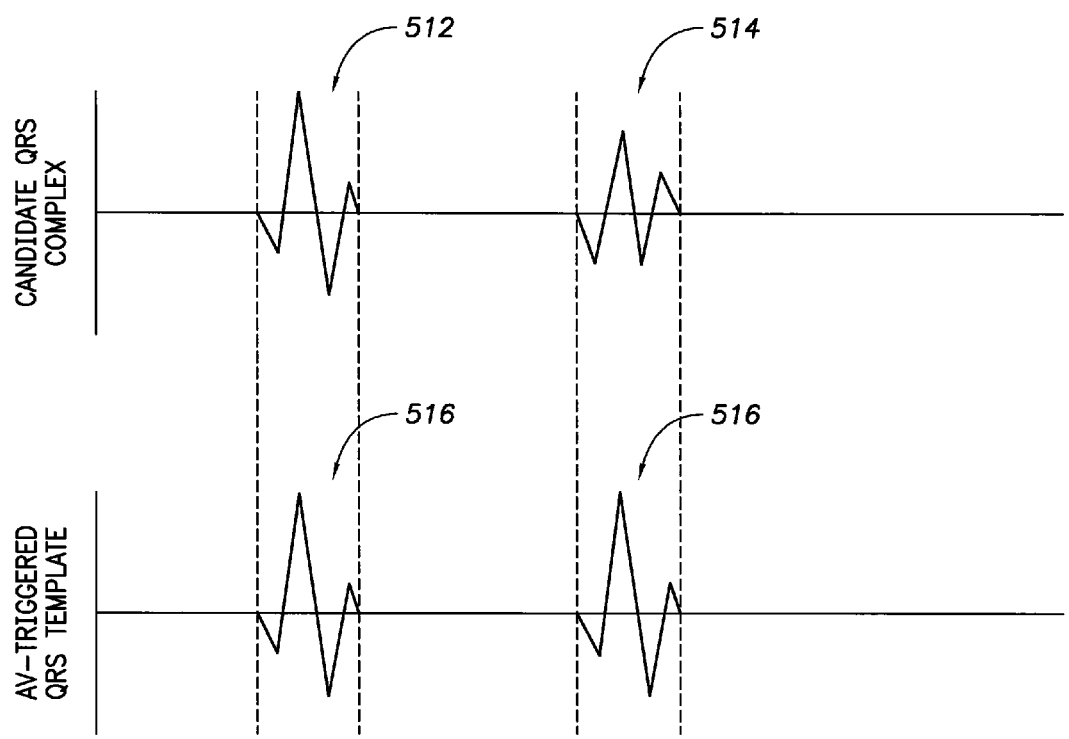
FIG. 10 is a graph illustrating an exemplary QRS template for use in distinguishing QRS complexes arising due to interventricular conduction from those arising due to AV conduction, for use with the techniques of FIGS. 8-9.

Turning now to FIGS. 8-10, techniques for distinguishing QRS complexes arising due to interventricular conduction from QRS complexes arising due to AV conduction will now be described for the purposes of determining paced interventricular conduction delays (IVCD_RL and IVCD_LR). Beginning at step 400 of FIG. 8, the pacer/ICD delivers ventricular pacing pulses to a selected ventricular chamber (e.g. the RV) and, at step 402, detects the next QRS complex within the other ventricular chamber (e.g. the LV). At step 404, the pacer/ICD then distinguishes QRS complexes arising due to interventricular conduction (i.e. triggered by the pacing pulse) from QRS complexes arising due to AV conduction (i.e. triggered by P-waves in the atria) by comparing the detected QRS complexes against a suitable template. In one example, the template is representative of the shape or morphology of QRS complexes due to AV conduction.

At step 406, the pacer/ICD determines paced interventricular conduction delays (e.g. IVCD_RL and IVCD_LR) based on measured time delays between the ventricular pacing pulses and the QRS complexes arising due to interventricular conduction. Then, at step 408, the pacer/ICD delivers biventricular pacing during VVI, V00, D00 or other non-atrial tracking modes using VV pacing delays derived from the paced interventricular conduction delays (e.g. IVCD_RL and IVCD_LR) determined at step 406. As noted, VVI is often used during AF and so the technique of FIG. 8 is particularly well-suited for use during AF. However, the technique may be performed during any non-atrial tracking mode, include asynchronous modes such as V00 and D00, and is not limited for use during AF.

FIG. 9 provides a more detailed example wherein the technique of FIG. 8 is exploited during RV and LV pace tests. Beginning at step 500, the pacer/ICD delivers a sequence of RV pacing pulses and, at step 502, detects candidate QRS complexes within the LV. The RV pulses can be delivered at a rate set using the techniques of FIG. 5 so that the pacing interval is set shorter than 95-98% of the RR intervals on the RV channel. However, as the techniques of FIG. 9 will distinguish QRS complexes arising due to interventricular conduction from those due to AV conduction, it is less important that a high pacing rate be used during the RV pace test.

At step 504, the pacer/ICD compares the candidate LV QRS's against a template representative of an LV QRS due to AV conduction from atria. If the candidate LV QRS matches the template, as determined at step 506, the candidate LV QRS is rejected at step 508 (as being a QRS due to AV conduction) for the purposes of determining the IVCD_RL. Otherwise, the candidate LV QRS is accepted at step 510 as being a QRS due to interventricular conduction and counted for use in determining the IVCD_RL.

FIG. 10 illustrates a pair of candidate LV QRS complexes 512 and 514 are shown in FIG. 10 along with an exemplary template 516. As can be seen, the first candidate LV QRS 512 matches template 514 and hence is deemed to be a QRS due to AV conduction and is rejected for the purposes of determining the IVCD_RL. The second candidate LV QRS 514 does not match the template and hence is deemed to be a QRS due to interventricular conduction and is accepted for the purposes of determining the IVCD_RL.

Returning to FIG. 9, at step 518, the pacer/ICD measures IVCDs between RV pacing pulses and corresponding accepted LV QRS's and, at step 520, sets the IVCD_RL based on the measured IVCDs. As with the various RV pace examples described above, a number of individual IVCD_RL values can be averaged together to obtain a final IVCD_RL for use in setting the VV pacing delays. For example, IVCD_RL values obtained over a period of one minute or based on sixty RV pulses can be used to calculate an average.

Similar procedures are performed to conduct an LV pace test. As many of the steps are similar to those of the RV pace test, these steps will not be described in detail again. Briefly, at step 522, the pacer/ICD delivers LV pacing pulses and, at step 524, detects candidate QRS complexes within the RV. At step 526, the pacer/ICD compares the candidate RV QRS's against a template representative of an RV QRS due to AV conduction from atria. If the candidate RV QRS matches the template, as determined at step 528, the candidate RV QRS is rejected at step 530; otherwise it is accepted at step 532. At step 534, the pacer/ICD measures IVCDs between LV pacing pulses and corresponding accepted RV QRS and, at step 536, sets the IVCD_LR based on the measured IVCDs.

The techniques of FIGS. 8-10 can be used in conjunction with those of FIGS. 2-9 and vice versa, when appropriate. Furthermore, when appropriate, the various techniques described herein can be used in conjunction with the predecessor techniques set forth in the patent documents listed in the Summary. For example, when there is no AF, the predecessor techniques can be used to set AV/PV and VV delays.

When AF is detected, the techniques described herein can instead be used to set VV delays. Moreover, where appropriate, the various techniques described herein can be used in conjunction with other pacing therapy techniques, such as cardiac resynchronization therapy (CRT). Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. Also, for patients subject to AF, it may be appropriate to deliver dynamic atrial overdrive (DAO) to the atria. DAO is discussed in, for example, U.S. Pat. No. 6,519,493 to Florio et al., entitled "Methods and Apparatus for Overdrive Pacing Heart Tissue Using an Implantable Cardiac Stimulation Device."

Although primarily described with respect to examples having a pacer/ICD, other implantable medical devices may be equipped to exploit the techniques described herein such as CRT devices and CRT-D devices. For the sake of completeness, an exemplary pacer/ICD will now be described, which includes components for performing the functions and steps already described.

Exemplary Pacer/ICD

Figure 11:
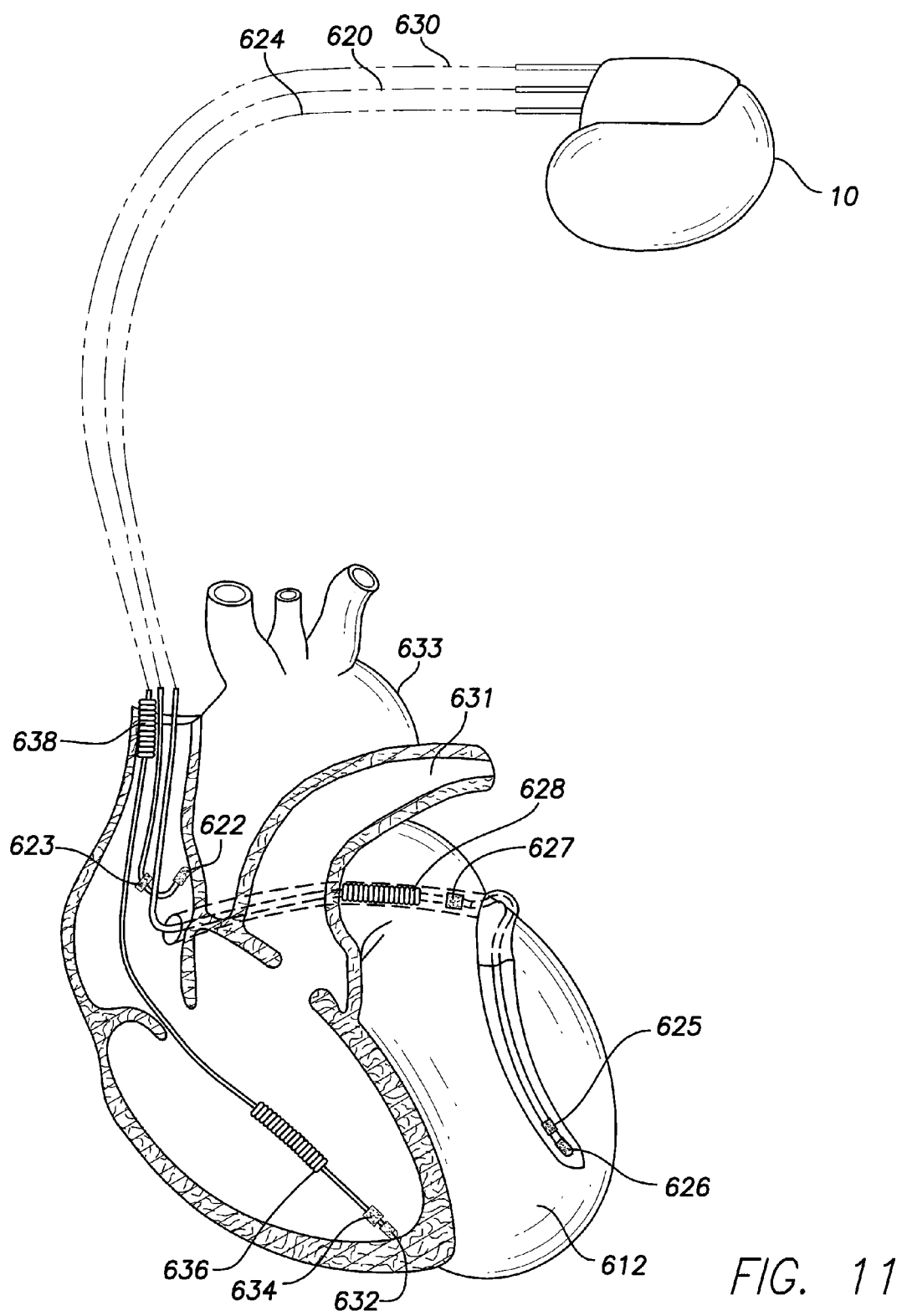
FIG. 11 is a simplified, partly cutaway view, illustrating the pacer/ICD of FIG. 1 along with at set of leads implanted into the heart of the patient.
Figure 12:
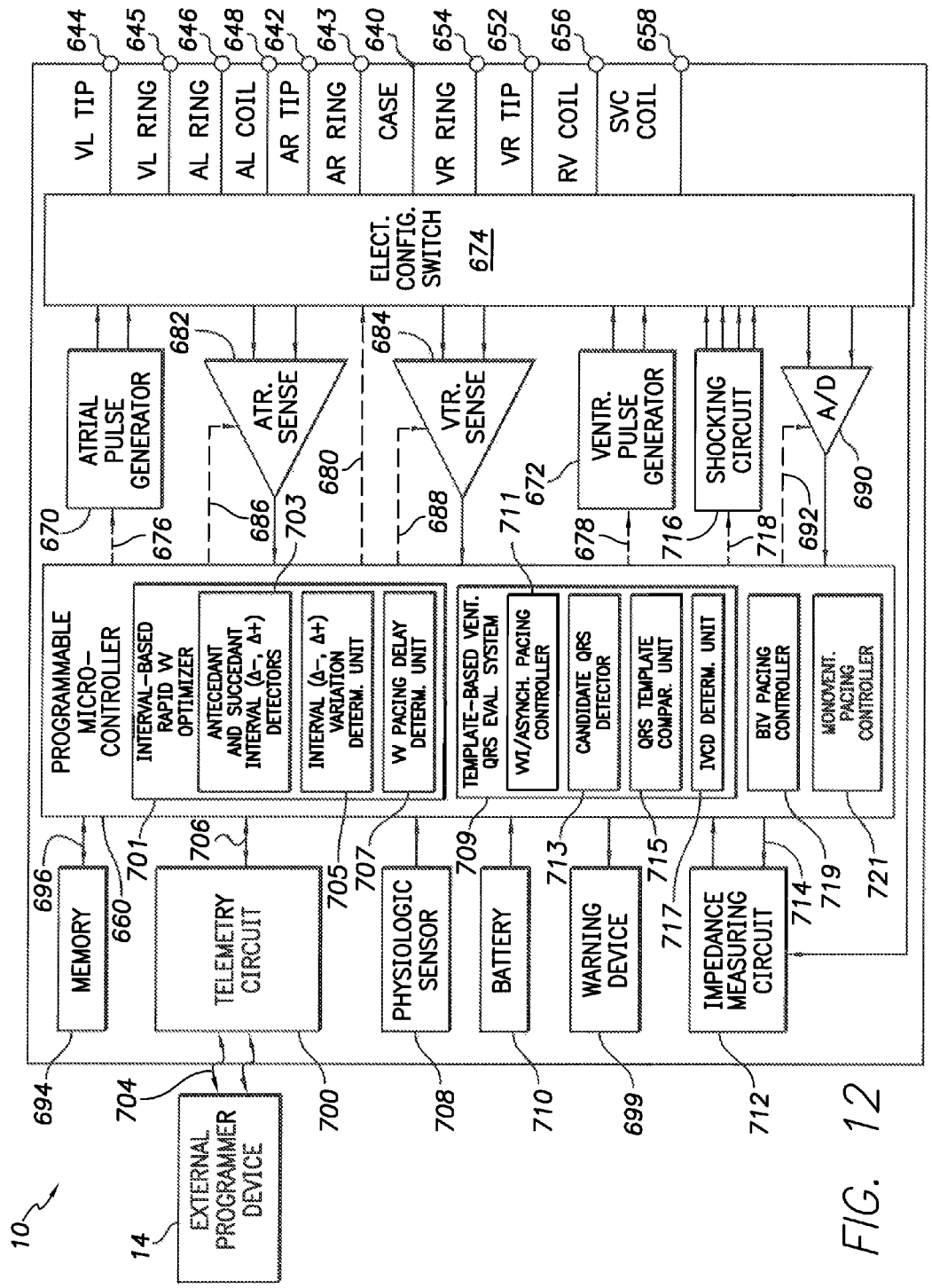
FIG. 12 is a functional block diagram of the pacer/ICD of FIG. 11, illustrating basic circuit elements that provide cardioversion, defibrillation and/or pacing stimulation in the heart an particularly illustrating an on-board optimization system for performing the optimization techniques of FIGS. 2-10.

With reference to FIGS. 11 and 12, a description of an exemplary pacer/ICD will now be provided. FIG. 11 provides a simplified block diagram of the pacer/ICD, which is a dual-chamber stimulation device capable of treating both fast and slow arrhythmias with stimulation therapy, including cardioversion, defibrillation, and pacing stimulation, and also capable of setting and using VV pacing delays, as discussed above. To provide other atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 624 is designed to receive atrial and ventricular cardiac signals and to deliver left ventricular pacing therapy using at least a left ventricular tip electrode 626 and a LV ring electrode 625, left atrial pacing therapy using at least a left atrial ring electrode 627, and shocking therapy using at least a left atrial coil electrode 628. With this configuration, biventricular pacing can be performed. Although only three leads are shown in FIG. 11, it should also be understood that additional leads (with one or more pacing, sensing and/or shocking electrodes) might be used and/or additional electrodes might be provided on the leads already shown.

A simplified block diagram of internal components of pacer/ICD 10 is shown in FIG. 12. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for pacer/ICD 10, shown schematically in FIG. 12, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 645, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left ventricular ring terminal ($V_L$ RING) 645, a left atrial ring terminal ($A_L$ RING) 646, and a left atrial shocking terminal ($A_L$ COIL) 648, which are adapted for connection to the left ventricular ring electrode 626, the left atrial ring electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($V_R$ COIL) 656, and an SVC shocking terminal (SVC COIL) 658, which are adapted for connection to the right ventricular tip electrode 632, right ventricular ring electrode 634, the $V_R$ coil electrode 636, and the SVC coil electrode 638, respectively.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 12, an atrial pulse generator 670 and a ventricular pulse generator 672 generate pacing stimulation pulses for delivery by the right atrial lead 620, the right ventricular lead 630, and/or the CS lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, CS lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the CS lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, VV delay, etc.) at which the atrial and ventricular pulse generators, 670 and 672, generate stimulation pulses. While shown as being included within pacer/ICD 10, it is to be understood that the physiologic sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 12. The battery 710 may vary depending on the capabilities of pacer/ICD 10. If the system only provides low voltage therapy, a lithium iodine or lithium copper fluoride cell typically may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 12, pacer/ICD 10 is shown as having an impedance measuring circuit 712, which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 712 is advantageously coupled to the switch 774 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

An internal warning device 699 may be provided for generating perceptible warning signals to the patient via vibration, voltage or other methods.

Insofar as ventricular pacing is concerned, the microcontroller includes an interval-based rapid VV optimizer 701 operative to perform or control the techniques of FIGS. 2-7, described above. The optimizer includes antecedent and succedent interval ($\Delta$-, $\Delta$+) detectors 703 and an interval ($\Delta$-, $\Delta$+) variation determination unit 705 operative during a V sense test. A VV pacing delay unit 707 determines a VV pacing delay based, at least in part, on values determined during the V sense test.

Insofar as template matching is concerned, the microcontroller also includes a template-based ventricular QRS evaluation system 709 operative to perform or control the techniques of FIGS. 8-10, described above. The QRS evaluation system includes a VVI/asynchronous pacing controller for controlling VVI, V00 and D00 pacing. A candidate QRS detector 713 detects candidate QRS complexes. A QRS template comparison unit 715 compares the candidate QRS's to a template, as already explained to distinguish QRS events arising via intraventricular conduction from those arising via AV conduction. An IVCD determination unit 717 determines IVCD_RL and IVCD_LR values during RV and LV pace tests.

Additionally, the microcontroller includes a biventricular pacing controller 719 and a monoventricular pacing controller 721 for controlling, respectively, biventricular and monoventricular pacing, as already described.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary External Programmer

Figure 13:
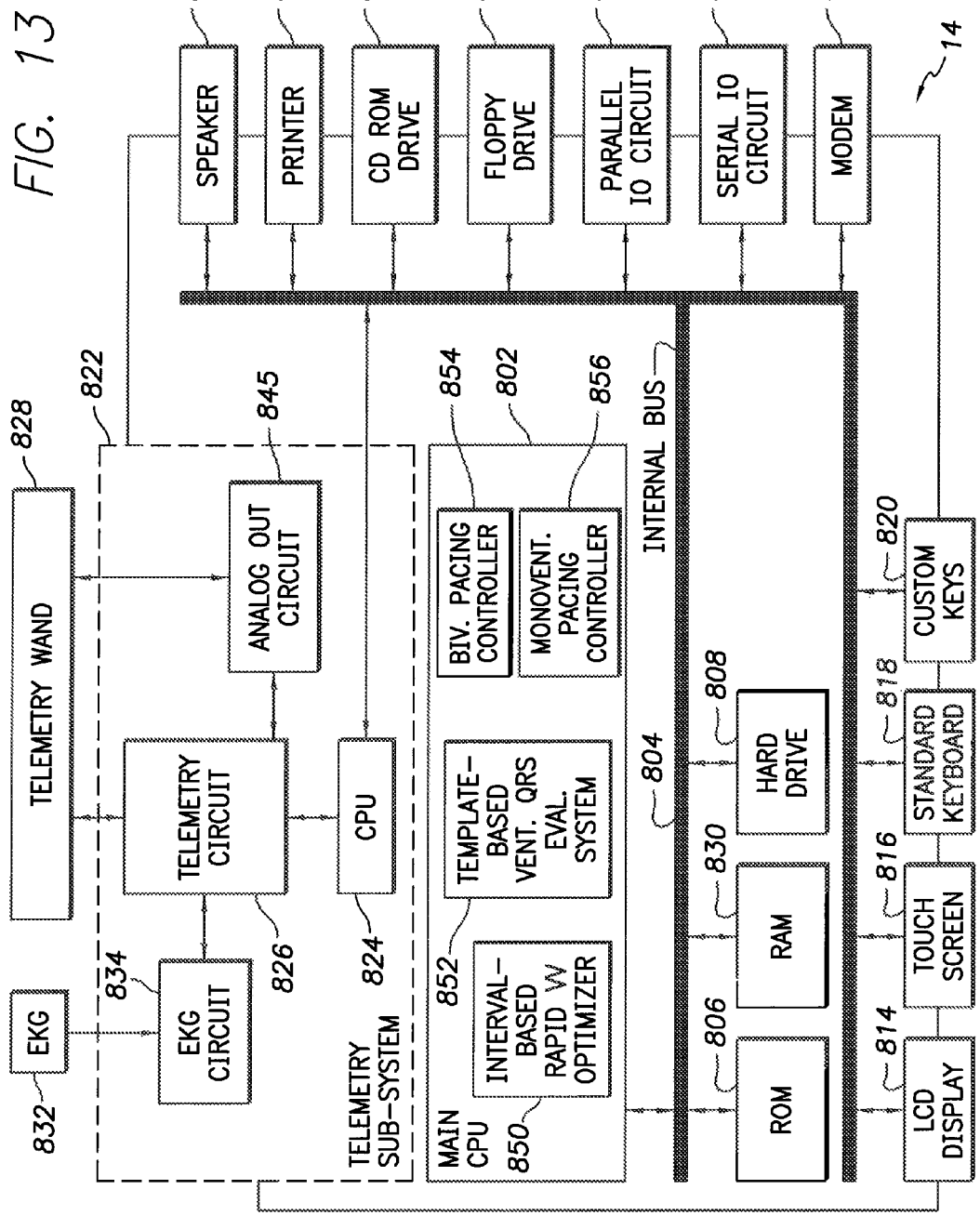
FIG. 13 is a functional block diagram illustrating components of the external device programmer of FIG. 1, and in particular illustrating a programmer-based optimization system for controlling the optimization techniques of FIGS. 2-10.

FIG. 13 illustrates pertinent components of an external programmer 14 for use in programming the pacer/ICD of FIG. 12 and for performing the above-described optimization techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 14 may also be capable of processing and analyzing data received from the implanted device and from the EKG leads to, for example, render preliminary diagnosis as to medical conditions of the patient or to the operations of the implanted device.

Now, considering the components of programmer 14, operations of the programmer are controlled by a CPU 802, which may be a generally programmable microprocessor or microcontroller or may be a dedicated processing device such as an application specific integrated circuit (ASIC) or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 814 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 816 overlaid on the LCD display or through a standard keyboard 818 supplemented by additional custom keys 820, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 14 to retrieve data stored within any implanted devices and to also retrieve EKG data from EKG leads, if any, coupled to the patient. To this end, CPU 802 transmits appropriate signals to a telemetry subsystem 822, which provides components for directly interfacing with the implanted devices, and the EKG leads. Telemetry subsystem 822 includes its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to telemetry wand 828, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 834 for receiving surface EKG signals from a surface EKG system 832. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 14 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 14, the implanted devices may be further controlled to transmit additional data in real time as it is detected by the implanted devices, such as additional IEGM data, lead impedance data, and the like. Additionally, or in the alternative, telemetry subsystem 822 receives EKG signals from EKG leads 832 via an EKG processing circuit 834. As with data retrieved from the implanted device itself, signals received from the EKG leads are stored within one or more of the storage devices of the external programmer. Typically, EKG leads output analog electrical signals representative of the EKG. Accordingly, EKG circuit 834 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 802, the programming commands are converted to specific programmable parameters for transmission to the implanted devices via telemetry wand 828 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 836.

Additionally, CPU 802 also preferably includes an interval-based rapid VV optimizer 850 operative to perform or control the techniques of FIGS. 2-7, described above. CPU 802 also preferably includes a template-based ventricular QRS evaluation system 852 operative to perform or control the techniques of FIGS. 8-10, described above. These components operate to analyze data received from the pacer/ICD, such as LV-IEGM and RV-IEGM data, and to determine optimal or preferred VV pacing delays for use in biventricular pacing or to determine the optimal ventricular chamber for use in monoventricular pacing. Pacing delay parameters and/or other pacing control information may then be transmitted to the pacer/ICD under the control of either a biventricular pacing controller 854 or a monoventricular pacing controller 856 to program the device to perform pacing in accordance with the optimal or preferred VV pacing delays or in accordance with monoventricular pacing control parameters.

Programmer/monitor 14 also includes a modem 838 to permit direct transmission of data to other programmers via the public switched telephone network (PSTN) or other interconnection line, such as a T1 line or fiber optic cable. Depending upon the implementation, the modem may be connected directly to internal bus 804 may be connected to the internal bus via either a parallel port 840 or a serial port 842. Other peripheral devices may be connected to the external programmer via parallel port 840 or a serial port 842 as well. Although one of each is shown, a plurality of input output (IO) ports might be provided. A speaker 844 is included for providing audible tones to the user, such as a warning beep in the event improper input is provided by the physician. Telemetry subsystem 822 additionally includes an analog output circuit 845 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 13 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for controlling the delivery of cardiac pacing therapy by an implantable cardiac rhythm management device for use with patients subject to atrial fibrillation, the method comprising:

detecting atrial fibrillation (AF), and in response to detecting AF;

determining a first degree of variation within intervals between ventricular events sensed by the device on a first channel and preceding ventricular events sensed on a second channel;

determining a second degree of variation within intervals between ventricular events sensed by the device on the first channel and subsequent ventricular events sensed on the second channel; and controlling ventricular pacing based, at least in part, on a comparison of the first and second degrees of variation.

2. The method of claim 1 wherein the first sensing channel is a right ventricular (RV) sensing channel and the second sensing channel is a left ventricular (LV) sensing channel.

3. The method of claim 2 wherein the ventricular events sensed on the first channel are right ventricular depolarization (RV QRS) events and the ventricular events sensed on the second channel are left ventricular depolarization (LV QRS) events.

4. The method of claim 1 wherein determining the first degree of variation includes:

detecting a first set of intervals ($\Delta-$) between the ventricular events sensed on the first channel and the preceding ventricular events sensed on the second channel; and determining a degree of variation within the first set of intervals ($\Delta-$).

5. The method of claim 4 wherein determining the second degree of variation includes:

detecting a second set of intervals ($\Delta+$) between the ventricular events sensed on the first channel and the preceding ventricular events sensed on the second channel; and determining a degree of variation within the second set of intervals ($\Delta+$).

6. The method of claim 5 wherein controlling ventricular pacing includes:

determining an interventricular pacing delay (VV) based, at least in part, on a comparison of the relative degrees of variation in the first and second sets of intervals ($\Delta-,\Delta+$); and controlling biventricular pacing based on the interventricular pacing delay (VV).

7. The method of claim 6 wherein determining the interventricular pacing delay (VV) based on the comparison of the sets of intervals includes:

comparing the degree of variation in the $\Delta-$ intervals to the degree of variation in the $\Delta+$ intervals to determine which has a smaller degree of variation;

deriving an intrinsic interventricular delay ($\Delta$) for the patient based on the set of intervals having the smaller degree of variation; and setting the interventricular pacing delay (VV) based, at least in part, on the intrinsic interventricular delay ($\Delta$).

8. The method of claim 7 wherein if the degree of variation in the $\Delta-$ intervals is smaller than the degree of variation in the $\Delta+$ intervals, then the intrinsic interventricular delay ($\Delta$) is set equal to negative $|\Delta-|$; and if the degree of variation in the Δ+ intervals is smaller than the degree of variation in the Δ− intervals, then the intrinsic interventricular delay (Δ) is set equal to positive |Δ+|.

9. The method of claim 7 further including:
determining a paced interventricular conduction delay from the RV to the LV of the patient (IVCD_RL);
determining a paced interventricular conduction delay from the LV to the RV of the patient (IVCD_LR);
determining an interventricular correction term (ε) from IVCD_RL and IVCD_LR; and
setting the interventricular pacing delay (VV) for the patient based on the intrinsic interventricular delay (Δ) and the interventricular correction term (ε).

10. The method of claim 1 wherein determining the first degree of variation includes determining a standard deviation in intervals measured between the ventricular events of the first channel and the preceding ventricular events of the second channel.

11. The method of claim 1 wherein determining the second degree of variation includes determining a median of intervals measured between the ventricular events of the first channel and the preceding ventricular events of the second channel and evaluating a number of intervals occurring within a range surrounding the median subject to a predetermined confidence interval.

12. The method of claim 5 wherein controlling ventricular pacing includes:
comparing the degree of variation in the Δ− intervals to the degree of variation in the Δ+ intervals to determine which has a smaller degree of variation;
if the degree of variation in the Δ− intervals is smaller than the degree of variation in the Δ+ intervals, then upon detection of a sensed QRS in the LV, immediately delivering a monoventricular pacing pulse to the RV; and
if the degree of variation in the Δ+ intervals is smaller than the degree of variation in the Δ− intervals, then upon detection of a sensed QRS in the RV, immediately delivering a monoventricular pacing pulse to the LV.

13. The method of claim 1 wherein all of the steps are performed by the implantable medical device.

14. A system for controlling the delivery of cardiac pacing therapy by an implantable cardiac rhythm management device for use with patients subject to atrial fibrillation (AF), the system comprising:
an AF detection unit operative to detect an episode of AF;
an interval variation determination unit operative in response to the detection of AF to determine a first degree of variation within intervals between ventricular events sensed on a first channel and preceding ventricular events sensed on a second channel;
the interval variation determination unit further operative to determine a second degree of variation between ventricular events sensed on the first channel and subsequent ventricular events sensed on the second channel; and
a ventricular pacing controller operative to control ventricular pacing based, at least in part, on a comparison of the first and second degrees of variation.

15. A system for controlling the delivery of cardiac pacing therapy by an implantable cardiac rhythm management device for use with patients subject to atrial fibrillation (AF), the system comprising:
means for detecting AF
means, responsive to a detection of AF, for determining a first degree of variation within intervals between ventricular events sensed by the device on a first channel and preceding ventricular events sensed on a second channel;
means for determining a second degree of variation within intervals between ventricular events sensed by the device on the first channel and subsequent ventricular events sensed on the second channel; and
means for controlling ventricular pacing based, at least in part, on a comparison of the first and second degrees of variation.

* * * * *